United States Patent
Morton et al.

(10) Patent No.: US 10,193,524 B2
(45) Date of Patent: Jan. 29, 2019

(54) RESONATOR STRUCTURE WITH ENHANCED REFLECTION OF SHEAR AND LONGITUDINAL MODES OF ACOUSTIC VIBRATIONS

(71) Applicant: Qorvo US, Inc., Greensboro, NC (US)

(72) Inventors: Rick Morton, Bend, OR (US); John Belsick, Bend, OR (US)

(73) Assignee: QORVO US, INC., Greensboro, NC (US)

( * ) Notice: Subject to any disclaimer, the term of this patent is extended or adjusted under 35 U.S.C. 154(b) by 281 days.

(21) Appl. No.: 15/297,508

(22) Filed: Oct. 19, 2016

(65) Prior Publication Data
US 2017/0117872 A1    Apr. 27, 2017

Related U.S. Application Data

(60) Provisional application No. 62/244,284, filed on Oct. 21, 2015.

(51) Int. Cl.
*H03H 9/17*    (2006.01)
*B06B 1/06*    (2006.01)
(Continued)

(52) U.S. Cl.
CPC ............ *H03H 9/17* (2013.01); *B06B 1/0685* (2013.01); *G01H 11/08* (2013.01);
(Continued)

(58) Field of Classification Search
CPC ...... H03H 9/17; H03H 9/175; H03H 9/02086; G10K 11/04
(Continued)

(56) References Cited

U.S. PATENT DOCUMENTS 4,640,756 A    2/1987    Wang et al.
8,409,875 B2    4/2013    Johal et al.
(Continued)

OTHER PUBLICATIONS

Kaitila, J. et al., "Measurement of Acoustical Parameters of Thin Films," 2006 IEEE Ultrasonics Symposium, Oct. 2-6, 2006, pp. 464-467.

(Continued)

*Primary Examiner* — Derek Rosenau
(74) *Attorney, Agent, or Firm* — Mueting, Raasch & Gebhardt, P.A.

(57) ABSTRACT

A solidly mounted resonator structure includes an multi-layer acoustic reflector structure and a piezoelectric material layer arranged between the first and second electrode structures to form an active region, with the acoustic reflector structure providing enhanced reflection of shear and longitudinal modes of acoustic vibrations. The solidly mounted resonator structure is configured for transduction of an acoustic wave including a longitudinal component and a shear component. The acoustic reflector structure includes multiple sequentially arranged differential acoustic impedance layer units each including a low acoustic impedance material layer in contact with a high acoustic impedance material layer. A frequency corresponding to a minimum transmissivity of a second harmonic resonance of a longitudinal response is substantially matched to a frequency corresponding to a minimum transmissivity of a third harmonic resonance of a shear response.

18 Claims, 12 Drawing Sheets

(51) Int. Cl.
| | |
|---|---|
| *G01H 11/08* | (2006.01) |
| *G01N 29/02* | (2006.01) |
| *G01N 29/036* | (2006.01) |
| *G01N 29/24* | (2006.01) |
| *G10K 11/04* | (2006.01) |
| *G10K 11/24* | (2006.01) |
| *H03H 9/02* | (2006.01) |

(52) U.S. Cl.
CPC ......... *G01N 29/022* (2013.01); *G01N 29/036* (2013.01); *G01N 29/2437* (2013.01); *G10K 11/04* (2013.01); *G10K 11/24* (2013.01); *H03H 9/02086* (2013.01); *H03H 9/175* (2013.01); *G01N 2291/012* (2013.01); *G01N 2291/014* (2013.01); *G01N 2291/0255* (2013.01); *G01N 2291/0256* (2013.01); *G01N 2291/0426* (2013.01)

(58) Field of Classification Search
USPC .................................................. 310/320, 321
See application file for complete search history.

(56) References Cited

U.S. PATENT DOCUMENTS

| | | | |
|---|---|---|---|
| 2004/0130847 | A1 | 7/2004 | Aigner et al. |
| 2004/0140869 | A1 | 7/2004 | Marksteiner et al. |
| 2004/0183400 | A1 | 9/2004 | Aigner et al. |
| 2008/0258845 | A1 | 10/2008 | Schmidhammer |
| 2009/0152983 | A1 | 6/2009 | Sinha et al. |
| 2012/0062068 | A1 | 3/2012 | Wathen et al. |
| 2014/0312994 | A1 | 10/2014 | Meltaus et al. |
| 2014/0333177 | A1* | 11/2014 | Guillou ............... H01L 41/0533 310/321 |
| 2015/0094000 | A1 | 4/2015 | Aigner et al. |

OTHER PUBLICATIONS

Lakin, K.M., "Thin Film Resonators and High Frequency Filters," TFR Technologies, Inc., Jun. 1, 2001, 18 pages.

Lakin, K.M., "Thin Film Resonators and Filters," 1999 IEEE Ultrasonics Symposium, 1999, pp. 895-906.

Marksteiner, S. et al., "Optimization of Acoustic Mirrors for Solidly Mounted BAW Resonators," 2005 IEEE Ultrasonics Symposium, Sep. 18-21, 2005, pp. 329-332.

Nakamura, Kiyoshi et al., "Theoretical Analysis of a Piezoelectric Thin Film Resonator With Acoustic Quarter-Wave Multilayers," Proceedings of the 1998 IEEE International Frequency Control Symposium, May 1998, IEEE, pp. 876-881.

Newell, W. E., "Face-Mounted Piezoelectric Resonators," Proceedings of the IEEE, vol. 53, No. 6, Jun. 1965, pp. 575-581.

Pensala, Tuomas, "Thin Film Bulk Acoustic Wave Devices: Performance Optimization and Modeling," Dissertation, Aalto University, Feb. 25, 2011, VTT Publications 756, 108 pages.

Salgar, Sushant et al., "Modeling and Simulation of the Thin Film Bulk Acoustic Resonator," 2002 IEEE International Frequency Control Symposium and PDA Exhibition, May 29-31, 2002, pp. 40-44.

Thalhammer, Robert et al., "Energy loss mechanisms in SMR—type BAW devices," IEEE MTT-S International Microwave Symposium digest, vol. 1, 2005, pp. 225-228.

Wang, J.S. et al., "Sputtered C-Axis Inclined Piezoelectric Films and Shear Wave Resonators," IEEE 37th Annual Symposium on Frequency Control, 1983, IEEE, pp. 144-150.

Link, Mathias, "Study and realization of shear wave mode solidly mounted film bulk acoustic resonators (FBAR) made of c-axis inclined zinc oxide (ZnO) thin films: application as gravimetric sensors in liquid environments," UniversitéHenri Poincaré—Nancy I, Thesis, Sep. 14, 2006, 225 pages.

International Patent Application No. PCT/US2016/057653, filed Oct. 19, 2016; International Search Report / Written Opinion dated Jan. 18, 2017; 11 pages.

Qorvo US, Inc., "Summary of Sales Activity of Predecessor to Applicant Concerning Tilted C-Axis Aluminum Nitride Products," Unpublished, Jan. 10, 2017, 1 page.

Munir, Farasat, "A Fast, Scalable Acoustic Resonator-Based Biosensor Array System for Simultaneous Detection of Multiple Biomarkers," Thesis, Georgia Institute of Technology, Dec. 2012, 160 pages.

Nirschl, Martin et al., "CMOS-Integrated Film Bulk Acoustic Resonators for Label-Free Biosensing," Sensors, vol. 10, No. 5, Apr. 27, 2010, pp. 4180-4193.

Villa-López, Farah Helue et al., "Design and modelling of solidly mounted resonators for low-cost particle sensing," Measurement Science and Technology, vol. 27, No. 2, Dec. 18, 2015, 13 pages.

\* cited by examiner

| Acoustic Reflector Design Details | | |
|---|---|---|
| Layer | Material | Thickness ($\lambda_L$) |
| R7 | $SiO_2$ | $0.77 * \lambda_L$ |
| R6 | W | $0.16 * \lambda_L$ |
| R5 | $SiO_2$ | $0.77 * \lambda_L$ |
| R4 | W | $0.16 * \lambda_L$ |
| R3 | $SiO_2$ | $0.77 * \lambda_L$ |
| R2 | W | $0.16 * \lambda_L$ |
| R1 | $SiO_2$ | $0.77 * \lambda_L$ |

*FIG. 6B*

| Acoustic Reflector Design Details | | |
|---|---|---|
| Layer | Material | Thickness ($\lambda_L$) |
| R13 | $SiO_2$ | $0.78*\lambda_L$ |
| R12 | AlN | $0.16*\lambda_L$ |
| R11 | $SiO_2$ | $0.78*\lambda_L$ |
| R10 | AlN | $0.16*\lambda_L$ |
| R9 | $SiO_2$ | $0.78*\lambda_L$ |
| R8 | AlN | $0.16*\lambda_L$ |
| R7 | $SiO_2$ | $0.78*\lambda_L$ |
| R6 | AlN | $0.16*\lambda_L$ |
| R5 | $SiO_2$ | $0.78*\lambda_L$ |
| R4 | AlN | $0.16*\lambda_L$ |
| R3 | $SiO_2$ | $0.78*\lambda_L$ |
| R2 | AlN | $0.16*\lambda_L$ |
| R1 | $SiO_2$ | $0.78*\lambda_L$ |

FIG. 7B

| Acoustic Reflector Design Details | | |
|---|---|---|
| Layer | Material | Thickness ($\lambda_L$) |
| R9 | $SiO_2$ | $0.76*\lambda_L$ |
| R8 | AlN | $0.16*\lambda_L$ |
| R7 | $SiO_2$ | $0.76*\lambda_L$ |
| R6 | AlN | $0.16*\lambda_L$ |
| R5 | $SiO_2$ | $0.76*\lambda_L$ |
| R4 | W | $0.16*\lambda_L$ |
| R3 | $SiO_2$ | $0.79*\lambda_L$ |
| R2 | W | $0.16*\lambda_L$ |
| R1 | $SiO_2$ | $0.79*\lambda_L$ |

FIG. 8B

| Low Impedance | | | High Impedance | | |
|---|---|---|---|---|---|
| Material | Density (g/cm$^3$) | Acoustic Z (x 10$^5$ g/cm$^2$ sec) | Material | Density (g/cm$^3$) | Acoustic Z (x 10$^5$ g/cm$^2$ sec) |
| Silicon Oxycarbide | 1.5 | 3.6 | Tantalum (IV) Oxide | 7.6 | 34.5 |
| Silicon Dioxide | 2.2 | 12.9 | Aluminum Nitride | 3.3 | 35.8 |
| Polymers | 1.0 – 1.5 | | Aluminum Oxide | 3.9 | 39.8 |
| | | | Molybdenum | 10.2 | 64.3 |
| | | | Tungsten | 19.4 | 100.6 |

FIG. 9

RESONATOR STRUCTURE WITH ENHANCED REFLECTION OF SHEAR AND LONGITUDINAL MODES OF ACOUSTIC VIBRATIONS

STATEMENT OF RELATED APPLICATIONS

This application claims the benefit of provisional patent application Ser. No. 62/244,284, filed Oct. 21, 2015, the disclosure of which is hereby incorporated herein by reference in its entirety.

TECHNICAL FIELD

The present disclosure relates to resonator structures, and particularly to resonator structures that reflect shear and longitudinal modes of acoustic vibrations.

BACKGROUND

A biosensor (or biological sensor) is an analytical device including a biological element and a transducer that converts a biological response into an electrical signal. Certain biosensors involve a selective biochemical reaction between a specific binding material (e.g., an antibody, a receptor, a ligand, etc.) and a target species (e.g., molecule, protein, DNA, virus, bacteria, etc.), and the product of this highly specific reaction is converted into a measurable quantity by a transducer. Other sensors may utilize a non-specific binding material capable of binding multiple types or classes of molecules or other moieties that may be present in a sample. The term "functionalization material" may be used herein to generally relate to both specific and non-specific binding materials. Transduction methods used with biosensors may be based on various principles, such as electrochemical, optical, electrical, acoustic, and so on. Among these, acoustic transduction offers a number of potential advantages, such as being real time, label free, and low cost, as well as exhibiting high sensitivity.

An acoustic wave device employs an acoustic wave that propagates through or on the surface of the specific binding material, whereby any changes to the characteristics of the propagation path affect the velocity and/or amplitude of the wave. The presence of functionalization material on or over an active region of an acoustic wave device permits an analyte to be bound to the functionalization material, thereby altering the mass being vibrated by the acoustic wave and altering the wave propagation characteristics (e.g., velocity, thereby altering resonance frequency). Changes in velocity can be monitored by measuring the frequency or phase characteristics of the sensor and can be correlated to a physical quantity being measured.

There has been a growing interest in electroacoustic devices for high-frequency sensing applications due to the potential for high sensitivity, resolution, and reliability. However, it is not trivial to apply electroacoustic technology in certain sensor applications—particularly sensors operating in liquid/viscous media (e.g., chemical and biochemical sensors)—since longitudinal and surface waves exhibit considerable acoustic leakage into such media, thereby inhibiting sensing capability.

In the case of a piezoelectric crystal resonator, an acoustic wave may embody a bulk acoustic wave (BAW) propagating through the interior (or "bulk") of a piezoelectric material. BAW devices typically involve transduction of an acoustic wave using electrodes arranged on opposing top and bottom surfaces of a piezoelectric material. In a BAW device, three wave modes can propagate, namely, one longitudinal mode (embodying longitudinal waves, also called compressional/extensional waves, and two shear modes (embodying shear waves, also called transverse waves), with longitudinal and shear modes respectively identifying vibrations where particle motion is parallel to or perpendicular to the direction of wave propagation. The longitudinal mode is characterized by compression and elongation in the direction of the propagation, whereas the shear modes consist of motion perpendicular to the direction of propagation with no local change of volume. Longitudinal and shear modes propagate at different velocities. In practice, these modes are not necessarily pure modes as the particle vibration, or polarization, is neither purely parallel nor purely perpendicular to the propagation direction. The propagation characteristics of the respective modes depend on the material properties and propagation direction respective to the crystal axis orientations. The ability to create shear displacements is beneficial for operation of acoustic wave devices with fluids because shear waves do not impart significant energy into fluids.

Certain piezoelectric thin films are capable of exciting both longitudinal and shear mode resonance, such as hexagonal crystal system piezoelectric materials including aluminum nitride (AlN) and zinc oxide (ZnO). To excite a wave including a shear mode using a standard sandwiched electrode configuration device, a polarization axis in a piezoelectric thin film must generally be non-perpendicular to (e.g., tilted relative to) the film plane. In biological sensing applications involving a liquid media, the shear component of the resonator is used because it is not damped completely by liquid loading. In this case, the piezoelectric material is grown with a c-axis orientation distribution that is non-perpendicular relative to a face of an underlying substrate to enable the shear component to be increased relative to the longitudinal component.

An electromechanical coupling coefficient is a numerical value that represents the efficiency of piezoelectric materials in converting electrical energy into acoustic energy for a given acoustic mode. Changing the c-axis angle of inclination for hexagonal crystal system piezoelectric materials causes variation in shear and longitudinal coupling coefficients. FIG. 1 embodies plots of shear coupling coefficient ($K_s$) and longitudinal coupling coefficient ($K_l$) each as a function of c-axis angle of inclination for AlN, although other piezoelectric materials show similar behavior. At certain angles (e.g., 46° and 90°) the longitudinal component is minimized and $K_l$ has a zero value, and at certain angles (e.g., 0° and 67°) the shear component is minimized and $K_s$ has a zero value. At all other angles of C-axis inclination, there exist both shear and longitudinal components of wave propagation. Devices built with C-axis angles that include both longitudinal and shear modes (e.g., at angles except for about 0°, 46°, 67°, and 90°) are referred to as quasi-shear mode devices.

Solidly mounted resonator BAW technology relies on a reflective structure (e.g., reflector array, acoustic mirror, etc.) underneath the resonator to help keep the energy confined within the resonating structure. In other words, the reflective structure reflects the acoustic energy back toward the resonator and isolates the resonator from the substrate. If the reflectivity of the reflective structure is not perfect, then energy will be lost from leakage into the substrate, which reduces the quality factor (Q) of the resonator. A typical reflector for a solidly mounted resonator BAW device includes alternating high and low acoustic impedance layers arranged between a substrate and a piezoelectric layer.

Quarter-wave thin-film technology is commonly used to create the reflective stack (e.g., sometimes referred to as a Bragg reflector or grating) using multiple layers of materials of different acoustic impedances. Providing alternating layers of materials with varying acoustic impedance promotes constructive interference of waves reflecting off the layer boundaries and creates a band of frequencies where high reflectivity (low transmissivity) is achieved. A typical transmissivity plot for a quarter-wave reflector design using a combination of five alternating layers of silicon dioxide [$SiO_2$] and tungsten [W] is shown in FIG. 2. This transmissivity plot exhibits shear wave leakage, since the plot is devoid of a region in which the shear response 2A (e.g., minimum shear transmissivity) and longitudinal response 2B (e.g., minimum longitudinal transmissivity) overlap significantly. Shear wave leakage that exists with a quarter-wave design (due to the lack of overlap of the responses) can reduce the obtainable Q of the resonator.

Conventional acoustic reflectors are not well-suited to provide high Q for the shear mode of an acoustic resonator in quasi-shear mode applications, while preventing both longitudinal and shear components from reflecting off the backside of the substrate (which would interfere with measurements obtained with a sensor incorporating the resonator). Conventional acoustic reflectors tend to exhibit excess transmissivity for at least one of the shear and longitudinal modes at the desirable operating frequencies for certain acoustic resonator-based sensing applications.

Accordingly, there is a need for improved acoustic reflectors capable of enhancing reflection of both shear and longitudinal energy for quasi-shear mode sensing applications.

SUMMARY

The present disclosure provides a solidly mounted resonator structure including a multi-layer reflector providing enhanced reflection of shear and longitudinal modes of acoustic vibrations. More specifically, the present disclosure provides a solidly mounted resonator structure including a piezoelectric material arranged between first and second electrodes and arranged over an acoustic reflector structure. The solidly mounted resonator structure is configured for transduction of an acoustic wave having a longitudinal wavelength $\lambda_L$ in an at least one active region. The piezoelectric material layer exhibits first and second harmonic resonances of a longitudinal response and exhibits first, second, and third harmonic resonances of a shear response. The acoustic reflector structure comprises a plurality of alternating high and low acoustic impedance layers, with layer thicknesses configured such that a frequency corresponding to a minimum transmissivity of the second harmonic resonance of the longitudinal response is substantially matched to a frequency corresponding to a minimum transmissivity of the third harmonic resonance of the shear response (e.g., low acoustic impedance layers having a thickness between $0.73\lambda_L$ to $0.82\lambda_L$ and high acoustic layers having a thickness between $0.13\lambda_L$ to $0.19\lambda_L$). The acoustic reflector structure preferably minimizes transmissivity for both shear and longitudinal modes (e.g., for a given number of layers).

In one aspect, a solidly mounted resonator structure comprises a substrate; an acoustic reflector structure arranged over the substrate and comprising a plurality of sequentially arranged differential acoustic impedance layer units, wherein each differential acoustic impedance layer unit of the plurality of sequentially arranged differential acoustic impedance layer units comprises a low acoustic impedance material layer in contact with a high acoustic impedance material layer; at least one first electrode structure arranged over at least a portion of the acoustic reflector structure; a piezoelectric material layer arranged over the at least one first electrode structure; and at least one second electrode structure arranged over at least a portion of the piezoelectric material layer; wherein at least one portion of the piezoelectric material layer is arranged between the at least one first electrode structure and the at least one second electrode structure to form at least one active region; the solidly mounted resonator structure is configured for transduction of an acoustic wave having a longitudinal wavelength $\lambda_L$ in the at least one active region; the low acoustic impedance material layer of each differential acoustic impedance layer unit comprises a thickness in a range of from $0.73\lambda_L$ to $0.82\lambda_L$, and the high acoustic impedance material layer of each differential acoustic impedance layer unit comprises a thickness in a range of from $0.13\lambda_L$ to $0.19\lambda_L$.

In certain embodiments, the acoustic reflector structure comprises at least two sequentially arranged differential acoustic impedance layer units and at least one additional low acoustic impedance material layer.

In certain embodiments, the piezoelectric material layer comprises a hexagonal crystal structure piezoelectric material that comprises a c-axis having an orientation distribution that is predominantly non-parallel to normal of a face of the substrate.

In certain embodiments, in each differential acoustic impedance layer unit, the high acoustic impedance material layer comprises an acoustic impedance that is at least about 2.5 times greater than an acoustic impedance of the low acoustic impedance material layer.

In certain embodiments, the substrate is arranged between a backside surface and the acoustic reflector structure, and the backside surface comprises a roughened surface configured to reduce or eliminate backside acoustic reflection.

In certain embodiments, the at least one first electrode structure comprises a plurality of first electrode structures; the at least one second electrode structure comprises a plurality of second electrode structures; a first portion of the solidly mounted resonator structure comprises a first solidly mounted bulk acoustic wave resonator device including a first active region arranged between one first electrode structure of the plurality of first electrode structures and one second electrode structure of the plurality of second electrode structures; and a second portion of the solidly mounted resonator structure comprises a second solidly mounted bulk acoustic wave resonator device including a second active region arranged between another first electrode structure of the plurality of first electrode structures and another second electrode structure of the plurality of second electrode structures. In certain embodiments, a solidly mounted bulk acoustic wave resonator chip is derived from the solidly mounted resonator structure. In certain embodiments, a sensor or microfluidic device incorporates the solidly mounted bulk acoustic wave resonator chip.

In one aspect, a solidly mounted resonator structure comprises a substrate; an acoustic reflector structure arranged over the substrate and comprising a plurality of sequentially arranged differential acoustic impedance layer units, wherein each differential acoustic impedance layer unit of the plurality of sequentially arranged differential acoustic impedance layer units comprises a low acoustic impedance material layer in contact with a high acoustic impedance material layer; at least one first electrode structure arranged over at least a portion of the acoustic reflector structure; a piezoelectric material layer arranged over the at least one first electrode structure; and at least one second electrode structure arranged over at least a portion of the piezoelectric material layer; wherein at least one portion of the piezoelectric material layer is arranged between the at least one first electrode structure and the at least one second electrode structure to form at least one active region; the solidly mounted resonator structure is configured for transduction of an acoustic wave including a longitudinal component and a shear component in the at least one active region, whereby the piezoelectric material layer exhibits first and second harmonic resonances of a longitudinal response and exhibits first, second, and third harmonic resonances of a shear response; and a frequency corresponding to a minimum transmissivity of the second harmonic resonance of the longitudinal response is substantially matched to a frequency corresponding to a minimum transmissivity of the third harmonic resonance of the shear response.

In certain embodiments, the frequency corresponding to a minimum transmissivity of the second harmonic resonance of the longitudinal response is within about 5% of the frequency corresponding to a minimum transmissivity of the third harmonic resonance of the shear response.

In certain embodiments, the acoustic reflector structure comprises first, second, and third low acoustic impedance material layers and comprises first and second high acoustic impedance material layers. The acoustic reflector structure is not specifically limited to the foregoing five-layer structure; accordingly, in certain embodiments, the limited to such layers, and in other embodiments, one or more additional low acoustic impedance material layers and/or one or more additional high acoustic impedance material layers may be provided.

In certain embodiments, the piezoelectric material layer comprises a hexagonal crystal structure piezoelectric material that comprises a c-axis having an orientation distribution that is predominantly non-parallel to normal of a face of the substrate.

In certain embodiments, the acoustic wave comprises a longitudinal wavelength $\lambda_L$; the low acoustic impedance material layer of each differential acoustic impedance layer unit comprises a thickness in a range of from $0.73\lambda_L$ to $0.82\lambda_L$, and the high acoustic impedance material layer of each differential acoustic impedance layer unit comprises a thickness in a range of from $0.13\lambda_L$ to $0.19\lambda_L$.

In certain embodiments, in each differential acoustic impedance layer unit, the high acoustic impedance material layer comprises an acoustic impedance that is at least about 2.5 times greater than an acoustic impedance of the low acoustic impedance material layer.

In certain embodiments, the substrate is arranged between a backside surface and the acoustic reflector structure, and the backside surface comprises a roughened surface configured to reduce or eliminate backside acoustic reflection.

In certain embodiments, the at least one first electrode structure comprises a plurality of first electrode structures; the at least one second electrode structure comprises a plurality of second electrode structures; a first portion of the solidly mounted resonator structure comprises a first solidly mounted bulk acoustic wave resonator device including a first active region arranged between one first electrode structure of the plurality of first electrode structures and one second electrode structure of the plurality of second electrode structures; and a second portion of the solidly mounted resonator structure comprises a second solidly mounted bulk acoustic wave resonator device including a second active region arranged between another first electrode structure of the plurality of first electrode structures and another second electrode structure of the plurality of second electrode structures. In certain embodiments, a solidly mounted bulk acoustic wave resonator chip is derived from the solidly mounted resonator structure. In certain embodiments, a sensor or microfluidic device incorporates the solidly mounted bulk acoustic wave resonator chip.

Those skilled in the art will appreciate the scope of the present disclosure and realize additional aspects thereof after reading the following detailed description of the preferred embodiments in association with the accompanying drawing figures.

BRIEF DESCRIPTION OF THE DRAWINGS

The accompanying drawing figures incorporated in and forming a part of this specification illustrate several aspects of the disclosure and, together with the description, serve to explain the principles of the disclosure.

FIG. 6B shows a table of exemplary thicknesses for each layer of the seven-layer acoustic reflector structure of FIG. 6A, with layer thicknesses being defined as fractional multiples of longitudinal wavelength $\lambda_L$.

FIG. 7B shows a table of exemplary thicknesses for each layer of the thirteen-layer acoustic reflector structure of FIG. 7A, with layer thicknesses being defined as fractional multiples of longitudinal wavelength $\lambda_L$.

FIG. 8B shows a table of exemplary thicknesses for each layer of the nine-layer acoustic reflector of FIG. 8A, with layer thicknesses being defined as fractional multiples of a longitudinal wavelength $\lambda_L$ of an acoustic wave reflected by the acoustic reflector.

FIG. 9 is a table of identifying exemplary low impedance materials and high impedance materials with density and acoustic impedance values, for use with acoustic reflector structures according to various embodiments of the present disclosure.

DETAILED DESCRIPTION

Figure 1:
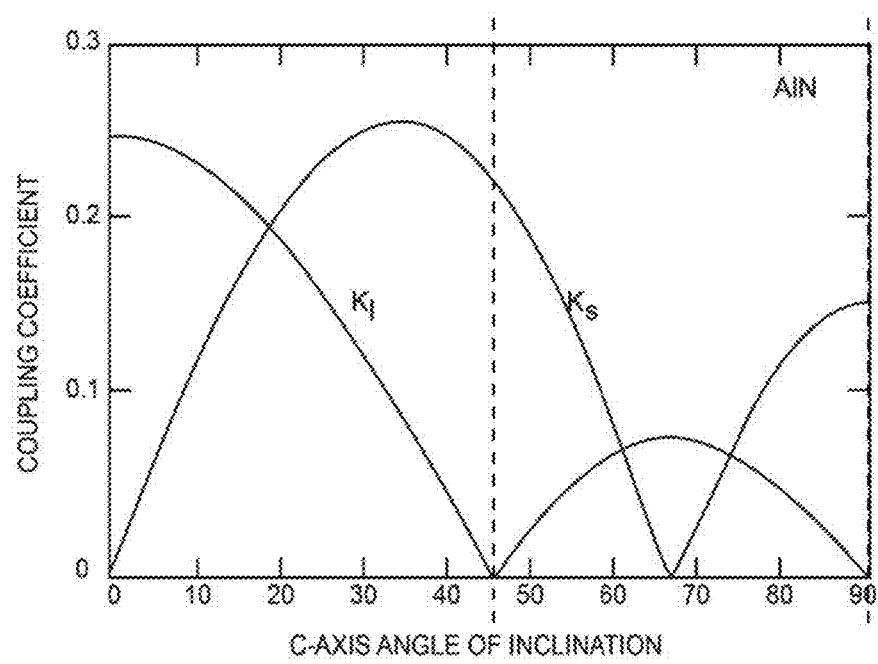
FIG. 1 is a plot of shear coupling coefficient ($K_s$) and longitudinal coupling coefficient ($K_l$) as a function of c-axis angle of inclination for aluminum nitride (AlN).
Figure 2:
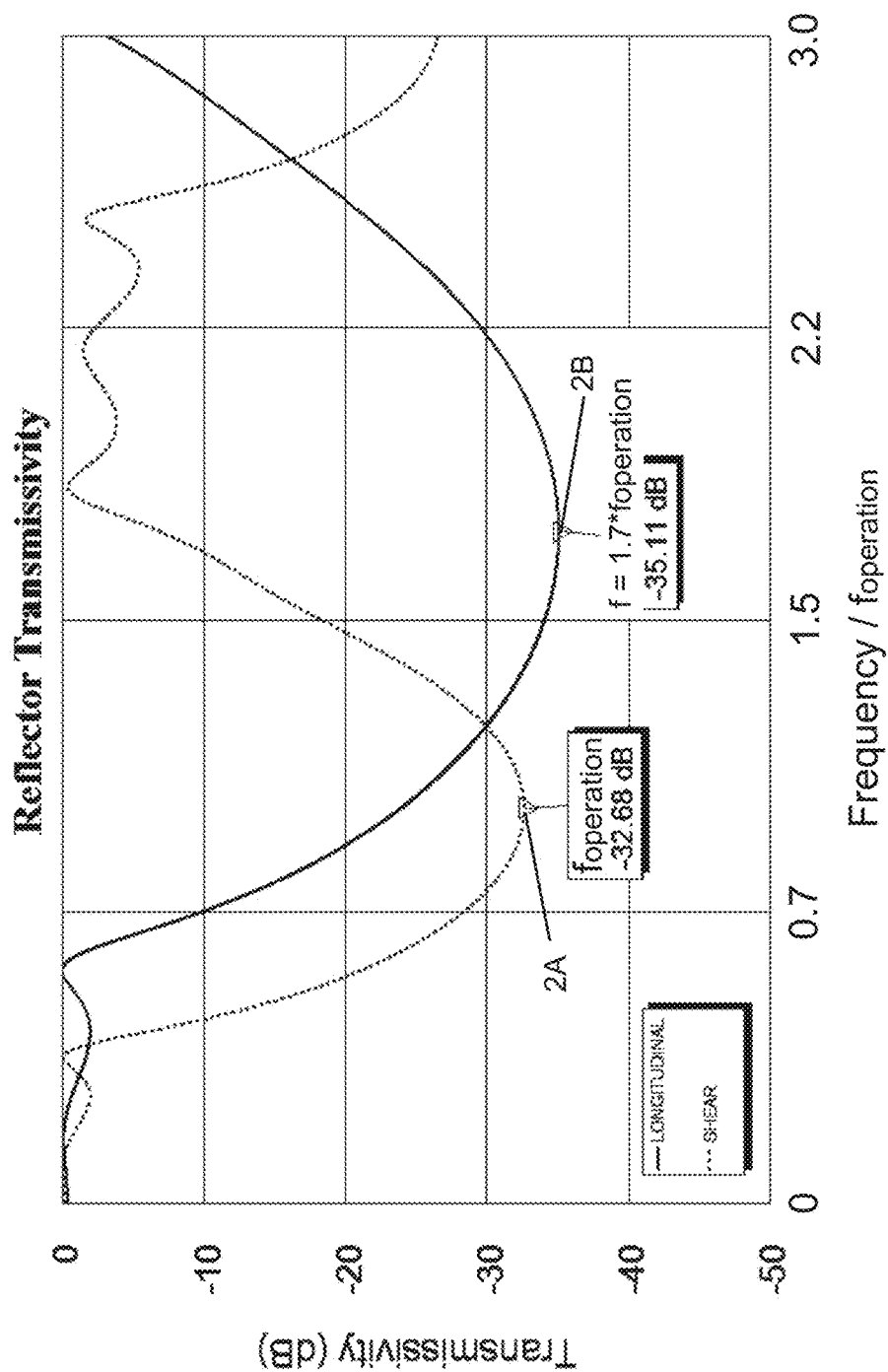
FIG. 2 is a transmissivity plot of reflector transmissivity as a function of frequency for a comparison structure including a five-layer quarter-wave reflector using alternating layers of silicon dioxide [$SiO_2$] and tungsten [W], with the plot illustrating a minimum shear transmissivity and a minimum longitudinal transmissivity at significantly different frequencies.

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

It should be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present disclosure. As used herein, the term "and/or" includes any and all combinations of one or more of the associated listed items.

It should also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

It should be understood that, although the terms "upper," "lower," "bottom," "intermediate," "middle," "top," and the like may be used herein to describe various elements, these elements should not be limited by these terms. These terms are only used to distinguish one element from another. For example, a first element could be termed an "upper" element and, similarly, a second element could be termed an "upper" element depending on the relative orientations of these elements, without departing from the scope of the present disclosure.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises," "comprising," "includes," and/or "including" when used herein specify the presence of stated features, integers, steps, operations, elements, and/or components but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having meanings that are consistent with their meanings in the context of this specification and the relevant art and will not be interpreted in an idealized or overly formal sense unless expressly so defined herein.

The present disclosure provides a solidly mounted resonator structure including a multi-layer reflector providing enhanced reflection of shear and longitudinal modes of acoustic vibrations. More specifically, the present disclosure provides a solidly mounted resonator structure including a piezoelectric material arranged between first and second electrodes and arranged over an acoustic reflector structure. The solidly mounted resonator structure is configured for transduction of an acoustic wave having a longitudinal wavelength $\lambda_L$ in the at least one active region. The piezoelectric material layer exhibits first and second harmonic resonances of a longitudinal response and exhibits first, second, and third harmonic resonances of a shear response. The acoustic reflector structure comprises a plurality of alternating high and low acoustic impedance layers, with layer thicknesses configured such that a frequency corresponding to a minimum transmissivity of the second harmonic resonance of the longitudinal response is substantially matched to a frequency corresponding to a minimum transmissivity of the third harmonic resonance of the shear response (e.g., low acoustic impedance layers having a thickness between $0.73\lambda_L$ to $0.82\lambda_L$ and high acoustic layers having a thickness between $0.13\lambda_L$ to $0.19\lambda_L$).

The acoustic reflector structure can be used with acoustic resonators arranged for quasi shear mode operation and configured for use with liquids, such as in sensing presence and/or concentration of one or more analytes in liquids or other viscous media. The acoustic reflector structure preferably minimizes transmissivity for both shear and longitudinal modes (e.g., for a given number of layers). The acoustic reflector structure utilizes overlapping harmonics of the reflector structure's transmissivity characteristics, which are a result of the different shear and longitudinal acoustic velocities of the materials. In certain embodiments, a variety of types of reflector structure designs could be used but may be altered such that the two layers closest to the resonator are configured to provide desirable levels of transmissivity and temperature compensation. Acoustic reflector structures disclosed herein are applicable across different materials systems for achieving high Q quasi-shear resonator performance required for liquid-sensing applications.

Figure 3A:
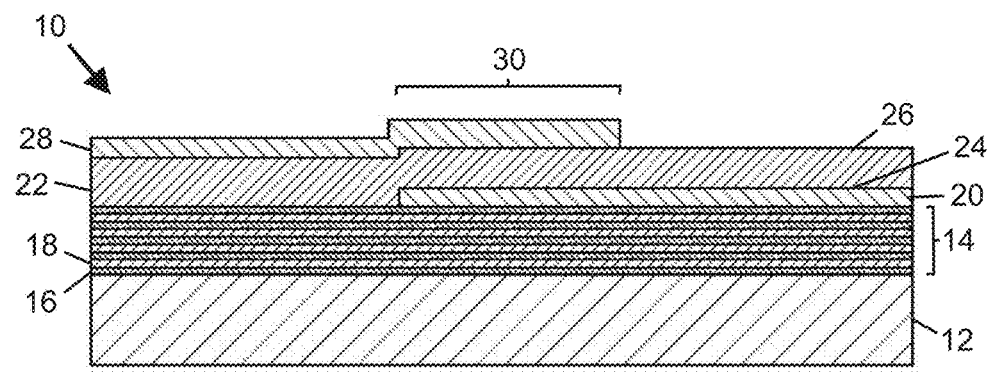
FIG. 3A is a schematic cross-sectional view of a portion of a bulk acoustic wave (BAW) micro-electro-mechanical systems (MEMS) resonator device including a multi-layer acoustic reflector structure according to one embodiment of the present disclosure.

FIG. 3A is a schematic cross-sectional view of a portion of a bulk acoustic wave micro-electro-mechanical systems (MEMS) resonator device 10 including a multi-layer acoustic reflector structure according to one embodiment of the present disclosure. The bulk acoustic wave MEMS resonator device 10 includes a substrate 12 (e.g., typically silicon or another semiconductor material), an acoustic reflector 14 arranged over the substrate 12, a piezoelectric material 22, and bottom and top side electrodes 20, 28. The bottom side electrode 20 is arranged along a portion of a lower surface 24 of the piezoelectric material 22 (between the acoustic reflector 14 and the piezoelectric material 22), and the top side electrode 28 is arranged along a portion of an upper surface 26 of the piezoelectric material 22. An area in which the piezoelectric material 22 is arranged between overlapping portions of the top side electrode 28 and the bottom side electrode 20 is considered an active region 30 of the resonator device 10. The acoustic reflector 14 serves to reflect acoustic waves and therefore reduce or avoid their dissipation in the substrate 12. The acoustic reflector 14 includes alternating thin layers 16, 18 of different materials (e.g., silicon oxycarbide [SiOC], silicon nitride [Si₃N₄], silicon dioxide [SiO₂], aluminum nitride [AlN], tungsten [W], and molybdenum [Mo]) deposited over the substrate 12. Steps for forming the resonator device 10 may include depositing the layers 16, 18 of the acoustic reflector 14 over the substrate 12, followed by deposition of the bottom side electrode 20, followed by growth (e.g., via sputtering or other appropriate methods) of the piezoelectric material 22, followed by deposition of the top side electrode 28.

The acoustic reflector 14 comprises alternating layers of low acoustic impedance material layers 16 and high acoustic impedance material layers 18, with the top and bottom layers of the acoustic reflector 14 being low acoustic impedance material layers 16. Each pair of one low acoustic impedance material layer 16 and an adjacent high acoustic impedance material layer 18 may be considered an acoustic impedance layer unit, with the acoustic reflector 14 including multiple acoustic impedance layer units. In certain embodiments, the high acoustic impedance material layer 18 comprises an acoustic impedance that is at least about 2.5 times greater than an acoustic impedance of the low acoustic impedance material layer 16 of a differential acoustic impedance layer unit.

In certain embodiments, the thicknesses of the low acoustic impedance material layers 16 and high acoustic impedance material layers 18 are configured to minimize transmissivity of longitudinal and shear modes of acoustic vibrations. As explained in more detail hereinafter, the thicknesses of the high acoustic impedance material layers 18 and low acoustic impedance material layers 16 are configured such that a frequency corresponding to a minimum transmissivity of the second harmonic resonance of the longitudinal response is substantially matched (or substantially similar) to a frequency corresponding to a minimum transmissivity of the third harmonic resonance of the shear response (e.g., low acoustic impedance material layers 16 having a thickness between $0.73\lambda_L$ to $0.82\lambda_L$ and high acoustic layers 18 having a thickness between $0.13\lambda_L$ to $0.19\lambda_L$, wherein $\lambda_L$ represents a longitudinal wavelength of an acoustic wave in the at least one active region. In certain embodiments, the frequency corresponding to a minimum transmissivity of the second harmonic resonance of the longitudinal response is within about 5%, about 4%, about 3%, about 2%, or about 1% (e.g., substantially matched to) the frequency corresponding to a minimum transmissivity of the third harmonic resonance of the shear response. In other words, the acoustic reflector is configured to provide harmonic overlap at a desired frequency range between the second harmonic of the shear transmissivity response and the third harmonic of the longitudinal transmissivity response, which is a result of the acoustic velocity differences for the shear and longitudinal modes in a given material (e.g., $V_S/V_L$ in a range of from about 0.56 to about 0.63). Such response is provided by multiple differential acoustic impedance layer units with thickness ranges as disclosed and claimed herein. In certain embodiments, the low acoustic impedance material layers 16 are all of the same thickness (e.g., a first thickness) and high acoustic impedance material layers 18 are all of the same thickness (e.g., a second thickness). In certain embodiments, the low acoustic impedance material layers 16 are not all of the same thickness and/or the high acoustic impedance material layers 18 are not all of the same thickness.

In certain embodiments, as explained in more detail hereinafter, the solidly mounted resonator structure incorporating an acoustic reflector 14 disclosed herein is part of a liquid-based sensor, with the acoustic reflector 14 being configured to reflect longitudinal modes and/or shear modes of acoustic vibrations toward the active region of a resonator structure, thereby preventing or at least substantially reducing dissipation of shear and longitudinal modes in a substrate of the solidly mounted resonator structure. This reduces or eliminates backside reflections of shear and longitudinal modes of acoustic vibrations from the substrate 12 (e.g., Si substrate), which can interfere with sensor measurements. Further, in certain embodiments the substrate 12 is arranged between a backside surface of the resonator device and the acoustic reflector 14, and the backside surface (e.g., embodying a surface of the substrate) is roughened to further reduce or eliminate backside acoustic reflection.

Figure 3B:
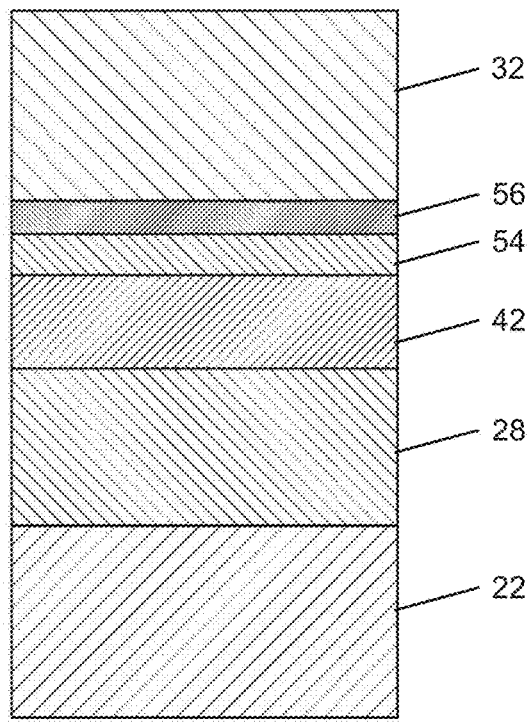
FIG. 3B is a schematic cross-sectional view of an upper portion of a bulk acoustic wave MEMS resonator device including a top side electrode overlaid with a hermeticity layer, an interface layer, a self-assembled monolayer, and a functionalization material layer according to one embodiment.

The bulk acoustic wave MEMS resonator device 10 shown in FIG. 3A lacks any layers (e.g., including functionalization material) overlying the active region 30 that would permit the device 10 to be used as a biochemical sensor. If desired, at least portions of a bulk acoustic wave MEMS resonator device 10 according to FIG. 3A (e.g., including the active region 30) may be overlaid with various layers. As shown in FIG. 3B, a piezoelectric layer 22 and a top side electrode 28 may be overlaid with a hermeticity layer 42 (e.g., to protect the top side electrode 28 from corrosion in a liquid environment), an interface layer 54 (e.g., to enable attachment of a functionalization material), and a functionalization material layer 32, which may include specific binding material or non-specific binding material. In certain embodiments, a self-assembled monolayer (SAM) 56 may be deposited prior to the functionalization material layer 32 to facilitate attachment of the functionalization material. In certain embodiments, one or more blocking materials may be applied during fabrication, such as over portions of an interface layer to prevent localized attachment of one or more subsequently deposited layers or (if applied over selected regions of a SAM or a functionalization material) to prevent analyte capture in regions not overlying an active region.

In certain embodiments, photolithography may be used to promote patterning of interface material or blocking material over portions of a MEMS resonator device. Photolithography involves use of light to transfer a geometric pattern from a photomask to a light-sensitive chemical photoresist on a substrate, and is a process well known to those of ordinary skill in the semiconductor fabrication art. Typical steps employed in photolithography include wafer cleaning, photoresist application (involving either positive or negative photoresist), mask alignment, and exposure and development. After features are defined in photoresist on a desired surface, an interface layer may be patterned by etching in one or more gaps defined in a photoresist layer, and the photoresist layer may be subsequently removed (e.g., using a liquid photoresist stripper, by ashing via application of an oxygen-containing plasma, or another removal process).

In certain embodiments, an interface layer (e.g., arrangeable between a top side electrode and a SAM) includes a hydroxylated oxide surface suitable for formation of an organosilane SAM. A preferred interface layer material including a hydroxylated oxide surface is $SiO_2$. Alternative materials incorporating hydroxylated oxide surfaces for forming interface layers include titanium dioxide [$TiO_2$] and tantalum pentoxide [$Ta_2O_5$]. Other alternative materials incorporating hydroxylated oxide surfaces will be known to those skilled in the art, and these alternatives are considered to be within the scope of the present disclosure.

In other embodiments, an interface layer (e.g., arrangeable between a top side electrode and a SAM), or at least one electrode that is devoid of an overlying interface layer, includes gold or another noble metal (e.g., ruthenium, rhodium, palladium, osmium, iridium, platinum, or silver) suitable for receiving a thiol-based SAM that may be overlaid with functionalization material.

In certain embodiments incorporating electrode materials subject to corrosion, a hermeticity layer may be applied between a top side electrode and an interface layer. The hermeticity layer may be unnecessary when noble metals (e.g., gold, platinum, etc.) are used for top side electrodes. If provided, the hermeticity layer preferably includes a dielectric material with a low water vapor transmission rate (e.g., no greater than 0.1 $g/m^2/day$). Following deposition of the hermeticity layer and the interface layer, a SAM may be formed over the interface layer, with the SAM including an organosilane material in certain embodiments. The hermeticity layer protects a reactive electrode material (e.g., aluminum or aluminum alloy) from attack in corrosive liquid environments, and the interface layer facilitates proper chemical binding of the SAM.

In certain embodiments, a hermeticity layer and/or an interface layer may be applied via one or more deposition processes such as atomic layer deposition (ALD), chemical vapor deposition, or physical vapor deposition. Of the foregoing processes, ALD is preferred for deposition of at least the hermeticity layer (and may also be preferable for deposition of the interface layer), due to its ability to provide excellent conformal coating with good step coverage over device features, so as to provide layer structures that are free of pinholes. Moreover, ALD is capable of forming uniformly thin layers that provide relatively little damping of acoustic vibrations that would otherwise result in degraded device performance. Adequacy of coverage is important for a hermeticity layer (if present) to avoid corrosion of the underlying electrode. If ALD is used for deposition of the hermeticity layer, then in certain embodiments the hermeticity layer may include a thickness in a range of from about 5 nm to about 100 nm, from about 5 nm to about 50 nm, or from about 10 nm to about 25 nm. In certain embodiments, hermeticity layer thickness is about 15 nm, or from about 12 nm to about 18 nm. Conversely, if another process such as chemical vapor deposition is used, then the hermeticity layer may include a thickness in a range of from about 80 nm to about 150 nm or more, or in a range of from about 80 nm to about 120 nm. Considering both of the foregoing processes, hermeticity layer thicknesses may range from about 5 nm to about 150 nm. If ALD is used for deposition of the interface layer, then the interface layer may include a thickness in a range of from about 5 nm to about 50 nm or from about 5 nm to about 15 nm. In certain embodiments, the interface layer may include a thickness of about 10 nm, or in a range of from about 8 nm to about 12 nm. Other interface layer thickness ranges and/or deposition techniques other than ALD may be used in certain embodiments. In certain embodiments, the hermeticity layer and the interface layer may be sequentially applied in a vacuum environment, thereby promoting a high-quality interface between the two layers.

If provided, a hermeticity layer may include an oxide, a nitride, or an oxynitride material serving as a dielectric material and having a low water vapor transmission rate (e.g., no greater than 0.1 ($g/m^2/day$)) according to certain embodiments. In certain embodiments, a hermeticity layer includes at least one of $Al_2O_3$ or SiN. In certain embodiments, an interface layer includes at least one of $SiO_2$, $TiO_2$, or $Ta_2O_5$. In certain embodiments, multiple materials may be combined in a single hermeticity layer, and/or a hermeticity layer may include multiple sublayers of different materials. Preferably, a hermeticity layer is further selected to promote compatibility with an underlying reactive metal (e.g., aluminum or aluminum alloy) electrode structure of an acoustic resonator structure. Although aluminum or aluminum alloys are frequently used as electrode materials in bulk acoustic wave resonator structures, various transition and post-transition metals can be used for such electrodes.

Following deposition of an interface layer (optionally arranged over an underlying hermeticity layer), a SAM is preferably formed over the interface layer. SAMs are typically formed by exposure of a solid surface to amphiphilic molecules with chemical groups that exhibit strong affinities for the solid surface. When an interface layer comprising a hydroxylated oxide surface is used, then organosilane SAMs are particularly preferred for attachment to the hydroxylated oxide surface. Organosilane SAMs promote surface bonding through silicon-oxygen (Si—O) bonds. More specifically, organosilane molecules include a hydrolytically sensitive group and an organic group and are therefore useful for coupling inorganic materials to organic polymers. An organosilane SAM may be formed by exposing the hydroxylated surface to an organosilane material in the presence of trace amounts of water to form intermediate silanol groups. These groups then react with free hydroxyl groups on the hydroxylated surface to covalently immobilize the organosilane. Examples of possible organosilane-based SAMs that are compatible with interface layers incorporating hydroxylated oxide surfaces include 3-glycidoxypropyltrimethoxysilane (GPTMS), 3-mercaptopropyltrimethoxysilane (MPTMS), 3-aminopropyltrimethoxysilane (APTMS), and octadecyltrimethoxysilane (OTMS), including their ethoxy- and chloro-variants. Additional silanes that may be used for SAMs include poly(ethylene glycol) (PEG) conjugated variants. Those skilled in the art will recognize that other alternatives exist, and these alternatives are considered to be within the scope of the present disclosure. An exemplary SAM may include a thickness in a range of at least 0.5 nm or more. Preferably, the SAM readily binds to the locally patterned interface layer but does not readily bind to other adjacent material layers (e.g., the hermeticity layer, a piezoelectric material, and/or a blocking material layer).

When an electrode(s) and/or interface layer comprising gold or another noble metal is used, then thiol-based (e.g., alkanethiol-based) SAMs may be used. Alkanethiols are molecules with an alkyl chain as the back bone, a tail group, and an S—H head group. Thiols may be used on noble metal interface layers due to the strong affinity of sulfur for these metals. Examples of thiol-based SAMs that may be used include, but are not limited to, 1-dodecanethiol (DDT), 11-mercaptoundecanoic acid (MUA), and hydroxyl-terminated (hexaethylene glycol) undecanethiol (1-UDT). These thiols contain the same backbone, but different end groups, namely, methyl ($CH_3$), carboxyl (COOH), and hydroxyl-terminated hexaethylene glycol (HO—$(CH_2CH_2O)_6$) for DDT, MUA, and 1-UDT, respectively. In certain embodiments, SAMs may be formed by incubating gold surfaces in thiol solutions using a suitable solvent, such as anhydrous ethanol.

Following formation of the SAM, the SAM may be biologically functionalized, such as by receiving at least one specific binding material. In certain embodiments, specific binding materials may be applied on or over the SAM using a microarray spotting needle or other suitable methods. In certain embodiments, the interface layer may be patterned (e.g., using photolithography for defining the interface layer) with a high dimensional tolerance over only a portion of a resonator structure (which includes a substrate), the SAM may be applied over the interface layer, and a subsequently applied specific binding material attaches only to the SAM. In certain embodiments, patterning of the interface layer may provide a higher dimensional tolerance for positioning of the specific binding material than could be attained by microarray spotting alone. Examples of specific binding materials include, but are not limited to, antibodies, receptors, ligands, and the like. The specific binding material is preferably configured to receive a predefined target species (e.g., molecule, protein, DNA, virus, bacteria, etc.). A functionalization layer including specific binding material may include a thickness in a range of from about 5 nm to about 1000 nm, or from about 5 nm to about 500 nm. In certain embodiments, an array of different specific binding materials may be provided over different active areas of a multi-resonator device (i.e., a resonator device including multiple active areas), optionally in combination with one or more active areas that are devoid of specific binding materials to serve as comparison (or "reference") regions. In certain embodiments, a functionalization material (e.g., providing chemical or biological functionalization) may provide non-specific binding utility.

In certain embodiments, a MEMS resonator device includes a bulk acoustic wave resonator device, and the piezoelectric material comprises a hexagonal crystal structure piezoelectric material (e.g., aluminum nitride or zinc oxide) that includes a c-axis having an orientation distribution that is predominantly non-parallel (and may also be non-perpendicular) to normal of a face of the substrate. Such a c-axis orientation distribution enables creation of shear displacements, which beneficially enable operation of the MEMS resonator device with liquids, such as in a sensor and/or microfluidic device. Methods for forming hexagonal crystal structure piezoelectric material including a c-axis having an orientation distribution that is predominantly non-parallel to normal of a face of a substrate are disclosed in U.S. patent application Ser. No. 15/293,063 filed on Oct. 13, 2016 and subsequently published as U.S. Patent Application Publication No. 2017/0110300 on Apr. 20, 2017, with the foregoing application hereby being incorporated by reference herein. Additional methods for forming piezoelectric material having an inclined c-axis orientation are disclosed in U.S. Pat. No. 4,640,756 issued on Feb. 3, 1987, with the foregoing patent hereby being incorporated by reference herein In certain embodiments, one or more piezoelectric material regions may have a c-axis with a longitudinal orientation.

Certain embodiments are directed to a fluidic device including a bulk acoustic wave MEMS resonator device as disclosed herein and including a fluidic passage arranged to conduct a liquid to contact at least one functionalization (e.g., specific binding) material (such as in FIG. 5, discussed hereinafter). Such a device may be microfluidic in scale and comprise at least one microfluidic channel (e.g., having at least one dimension, such as height and/or width, of no greater than about 500 microns, or about 250 microns, or about 100 microns). For example, following fabrication of a bulk acoustic wave MEMS resonator device and deposition of an interface layer and a SAM over portions thereof (optionally preceded by deposition of a hermeticity layer), a microfluidic device may be fabricated by forming one or more walls defining lateral boundaries of a microfluidic channel preferably containing the active region of at least one acoustic resonator, followed by application of a cover or cap layer to enclose the microfluidic channel. In certain embodiments, functionalization (e.g., specific binding) material may be applied after formation of walls of a microfluidic channel, but prior to application of the cover or cap layer. Walls of a microfluidic channel may be formed of any suitable material, such as laser-cut "stencil" layers of thin polymeric materials and/or laminates, optionally including one or more self-adhesive surfaces (e.g., adhesive tape). Optionally such walls may be formed prior to deposition of a SAM layer, functionalization layer, and/or blocking layers, with an SU-8 negative epoxy resist or other photoresist material. In certain embodiments, a cover or cap layer may be integrally formed with one or more walls (e.g., via molding or another suitable process) to define upper and lateral boundaries of at least one fluidic channel, and the integrally formed cover/wall structure may be applied (e.g., adhered or otherwise bonded) over at least a portion of a bulk acoustic wave resonator structure to enclose the at least one fluidic channel.

In certain embodiments, a chemical or biological blocking material may be applied over a portion of a SAM to prevent attachment of a functionalization (e.g., specific binding) material over one or more selected regions of a bulk acoustic wave resonator structure (e.g., one or more regions apart from an active region). The proper choice of a chemical or biological blocking material (e.g., blocking buffer) for a given analysis depends on the type of target species or analyte present in a sample. Various types of blocking buffers such as highly purified proteins (e.g., bovine serum albumin), serum, or milk may be used to block free sites on a SAM. Additional blockers include materials containing ethanolamine or polyethylene oxide (PEO). An ideal blocking buffer would bind to all potential sites of nonspecific interaction away from an active region. To optimize a blocking buffer for a particular analysis, empirical testing may be used to determine signal-to-noise ratio. No single chemical blocking material is ideal for every situation, since each antibody-antigen pair has unique characteristics.

Figure 4:
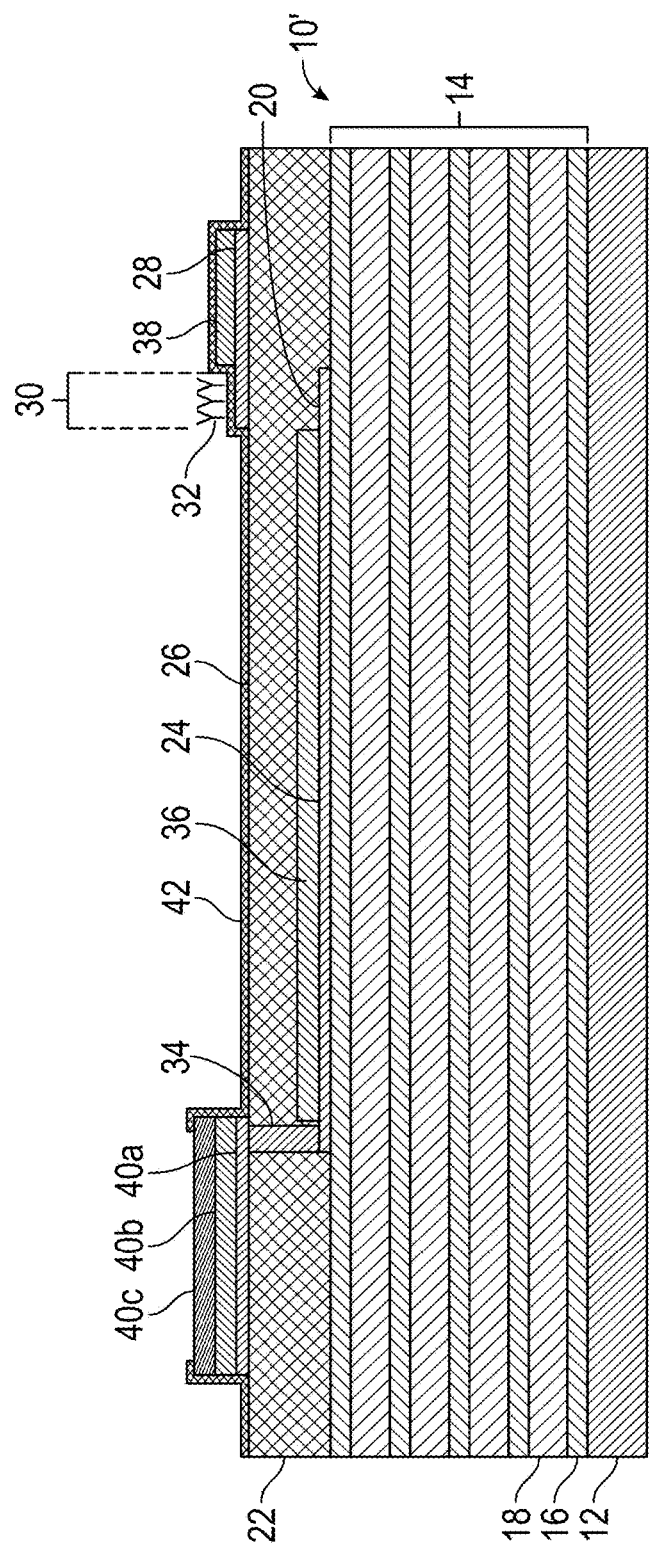
FIG. 4 is a schematic cross-sectional view of a portion of a BAW MEMS resonator device with overlying layers as well as an acoustic reflector structure including reflector layers of alternating high and low acoustic impedance according to one embodiment.

FIG. 4 is a schematic cross-sectional view of a portion of a bulk acoustic wave MEMS resonator device 10' incorporating an acoustic reflector 14 as disclosed herein according to one embodiment. The bulk acoustic wave MEMS resonator device 10' shown in FIG. 4 is similar to the bulk acoustic wave MEMS resonator device 10 illustrated in FIG. 3, except where otherwise noted. More specifically, the bulk acoustic wave MEMS resonator device 10' of FIG. 4 includes a substrate 12 (e.g., typically silicon or another semiconductor material), the acoustic reflector 14 arranged over the substrate 12, a piezoelectric material 22, and bottom and top side electrodes 20, 28. The bottom side electrode 20 is arranged along a portion of a lower surface 24 of the piezoelectric material 22 (between the acoustic reflector 14 and the piezoelectric material 22), and the top side electrode 28 is arranged along a portion of an upper surface 26 of the piezoelectric material 22. An area in which the piezoelectric material 22 is arranged between overlapping portions of the top side electrode 28 and the bottom side electrode 20 is considered an active region 30 of the bulk acoustic wave MEMS resonator device 10'. A functionalization (e.g., specific binding) material 32 is applied over the active region 30 to overlap at least a portion of the active region or substantially the entire active region 30. The acoustic reflector 14 comprises alternating layers of low acoustic impedance material layers 16 and high acoustic impedance material layers 18, forming multiple differential acoustic impedance layer units with thickness ranges as described herein.

As illustrated, the top electrode 28 is positioned above a rightmost end of the bottom side electrode 20, with piezoelectric material 22 arranged therebetween. To provide electric communication with the bottom side electrode 20, a conductive via 34 extends through the piezoelectric material 22 between a leftmost end of the bottom side electrode 20 and a contact pad 40a, which is positioned along the upper surface 26 of the piezoelectric material 22. FIG. 4 further illustrates a bottom electrode build-up layer 36 arranged over a central portion of the bottom side electrode 20, a top electrode build-up layer 38 arranged above a portion of the top side electrode 28, a contact pad build-up layer 40b arranged over the contact pad 40a, and an under bump metallization layer 40c positioned over the contact pad build-up layer 40b (and also over the contact pad 40a). The bottom electrode build-up layer 36, top electrode build-up layer 38, and/or contact pad build-up layer 40b may be optional in certain embodiments. If provided, the bottom electrode build-up layer 36 preferably has a reduced width compared with the bottom electrode 20 to prevent conductive communication with the conductive via 34 at the left end of the bottom electrode 20 and to avoid extension into the active region 30 at the right end of the bottom electrode 20. Similarly, if provided, the top electrode build-up layer portion 38 may be configured with a reduced width compared with the top electrode 28 to prevent overlap between the top electrode build-up layer portion 38 and the active region 30. The contact pad build-up layer 40b is positioned over the contact pad 40a.

A hermeticity layer 42 is positioned (e.g., by atomic layer deposition) over at least portions of exposed top and/or lateral surfaces of the piezoelectric material 22, top electrode 28, top electrode build-up layer 38, contact pad 40a, contact pad build-up layer 40b, and under bump metallization layer 40c. The hermeticity layer 42 may have one or more apertures therein, such as to provide access to the under bump metallization layer 40c. A functionalization material 32 is positioned over the active region 30 and over the hermeticity layer 42, with adhesion preferably aided by a self-assembled monolayer (not shown) arranged over an interface layer (not shown).

Figure 5:
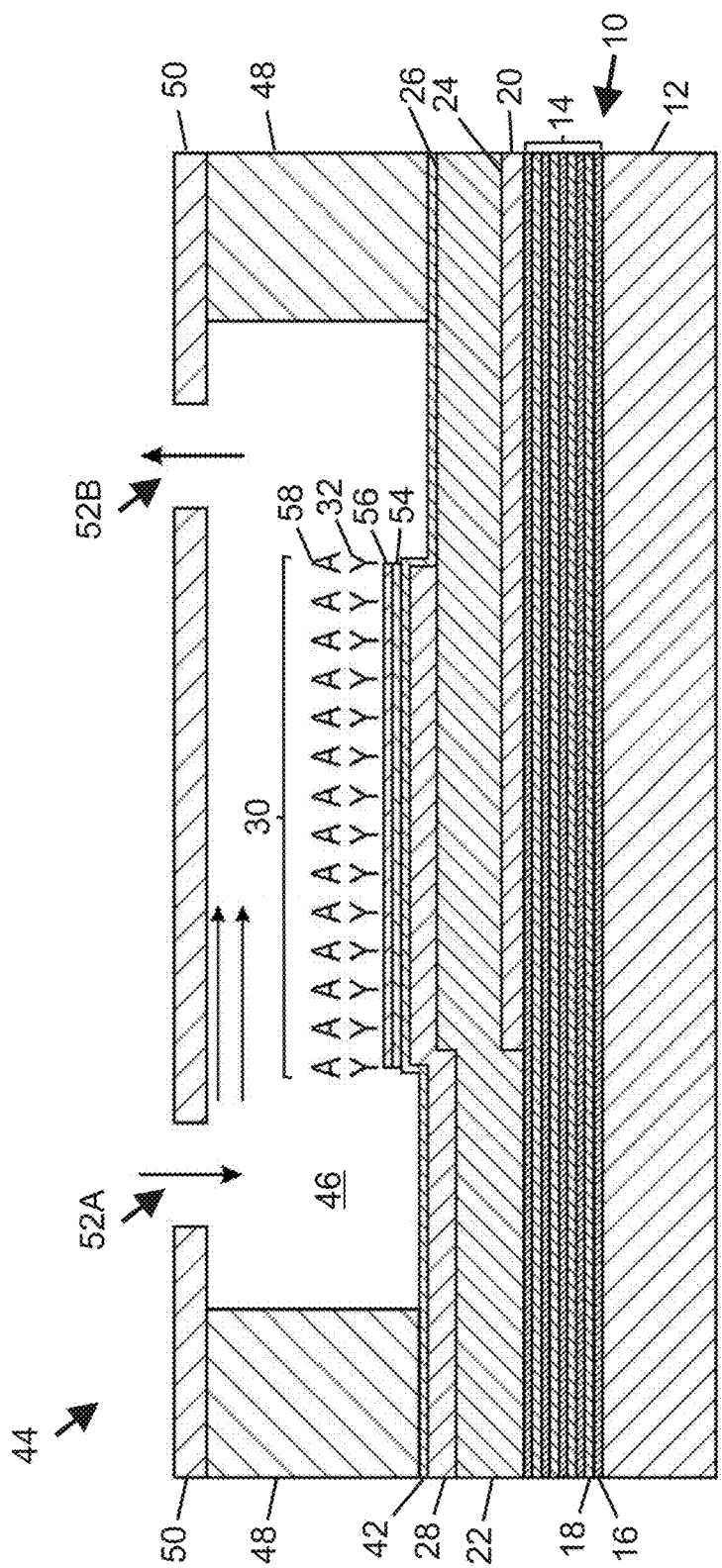
FIG. 5 is a schematic cross-sectional view of a portion of a fluidic device (e.g., a biochemical sensor device) including a microfluidic channel bounded from below by a BAW resonator structure, bounded laterally by walls, and bounded from above by a cover defining fluidic ports arranged along an upper or top surface of the fluidic device, according to one embodiment.

FIG. 5 is a schematic cross-sectional view of a portion of a fluidic device 44 (e.g., a biochemical sensor device) including a microfluidic channel 46 bounded from below by a bulk acoustic wave MEMS resonator structure 10, bounded laterally by walls 48, and bounded from above by a cover or cap layer 50 defining fluidic ports 52A, 52B in fluid communication with the microfluidic channel 46. In certain embodiments, the fluidic device 44 incorporates a solidly mounted bulk acoustic wave MEMS resonator structure as described in connection with FIGS. 3 and 4. As described previously, the bulk acoustic wave MEMS resonator structure 10 includes a substrate 12 overlaid with an acoustic reflector 14, and a bottom side electrode 20 arranged generally below a piezoelectric material 22 both overlying the acoustic reflector 14. The acoustic reflector includes multiple alternating low acoustic impedance material layers 16 and high acoustic impedance material layers 18 forming multiple differential acoustic impedance layer units with thickness ranges as disclosed herein. A top side electrode 28 extends over a portion of the piezoelectric material 22, wherein a portion of the piezoelectric material 22 arranged between the top side electrode 28 and the bottom side electrode 20 embodies an active region 30 of the bulk acoustic wave resonator structure. The top side electrode 28 and the piezoelectric material 22 are overlaid with a hermeticity layer 42. A portion of the hermeticity layer 42 registered with the active region 30 is further overlaid with an interface layer 54, a SAM 56, and functionalization (e.g., specific binding) material 32 arranged to bind a specified analyte 58. Walls 48 that are laterally displaced from the active region 30 extend upward from the interface layer 54 to define lateral boundaries of the microfluidic channel 46 containing the active region 30. Such walls 48 may be formed of any suitable material, such as a laser-cut "stencil" layer of thin polymeric materials and/or laminate materials, optionally including one or more self-adhesive surfaces (e.g. adhesive tape). Alternatively, the walls 48 may be formed of with an SU-8 negative epoxy resist or other photoresist material, optionally prior to deposition of the SAM 56, functionalization material 32, and chemical or biological blocking material. The cover or cap layer 50 defining upper surface fluidic ports 52A, 52B is further provided to provide an upper boundary for the microfluidic channel 46. The cover or cap layer 50 may be formed by defining ports (e.g., via laser cutting or water jet cutting) in a layer of an appropriate material (e.g., a substantially inert polymer, glass, silicon, ceramic, or the like), and adhering the cover or cap layer 50 to top surfaces of the walls 48.

In use of the fluidic device 44, a fluid sample may be supplied through the first fluidic port 52A, into the microfluidic channel 46 over the active region 30, and through the second fluidic port 52B to exit the microfluidic channel 46. As shown, an analyte 58 supplied by the fluid sample is bound to the functionalization (e.g., specific binding) material 32. When a bulk acoustic wave is induced in the active region 30 by supplying an electrical (e.g., alternating current) signal to the bottom and top side electrodes 20, 28, detection of a change in at least one of a frequency property or a phase property of the bulk acoustic wave resonator structure indicates a presence and/or quantity of target species (i.e., analyte) bound to the functionalization material 32.

Figure 6A:
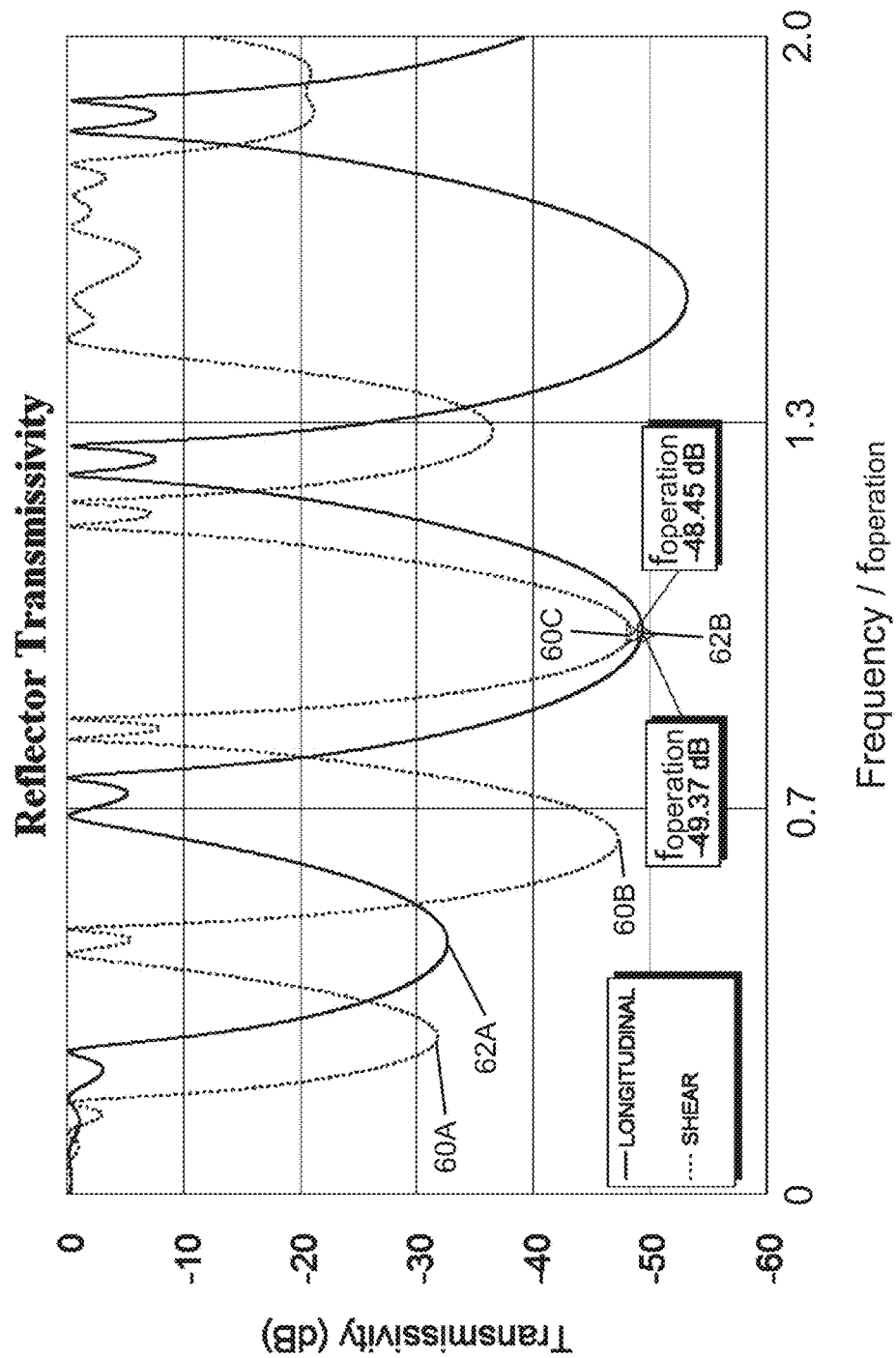
FIG. 6A shows an exemplary transmissivity plot of reflector transmissivity as a function of frequency for an acoustic reflector structure including seven alternating $SiO_2$/W layers, with thicknesses of the layers being configured to optimize both shear and longitudinal transmissivity at a desired frequency such that a minimum shear transmissivity at a third harmonic and a minimum longitudinal transmissivity at a second harmonic occur at substantially the same frequency.

FIG. 6A is an exemplary plot of reflector transmissivity as a function of frequency for a seven-layer acoustic reflector for a bulk acoustic wave resonator structure, with the acoustic reflector consisting of alternating layers of $SiO_2$ and W forming multiple differential acoustic impedance layer units. As shown, a shear response comprises a first harmonic 60A, a second harmonic 60B, and a third harmonic 60C, and a longitudinal response comprises a first harmonic 62A and a second harmonic 62B. The thicknesses of the reflector layers were configured to optimize both shear and longitudinal transmissivity at a desired frequency such that a minimum transmissivity of the third harmonic 60C of the shear response and a minimum transmissivity of the second harmonic 62B of the longitudinal response occur at substantially the same frequency, creating a significant overlap of the second harmonic 62B of the longitudinal response and third harmonic 60C of the shear response. The resulting acoustic reflector structure minimizes transmissivity for both shear and longitudinal modes (e.g., for a given number of layers).

FIG. 6B is a table of exemplary thicknesses for each layer of the seven-layer acoustic reflector described in connection with FIG. 6A. The layer thicknesses are defined as fractional multiples of the longitudinal wavelength $\lambda_L$. As shown, the low acoustic impedance material layers (R1, R3, R5, and R7) are all of the same material ($SiO_2$) and the same thickness ($0.77*\lambda_L$), and the high acoustic impedance material layers (R2, R4, R6) are all of the same material (W) and the same thickness ($0.16*\lambda_L$).

Figure 7A:
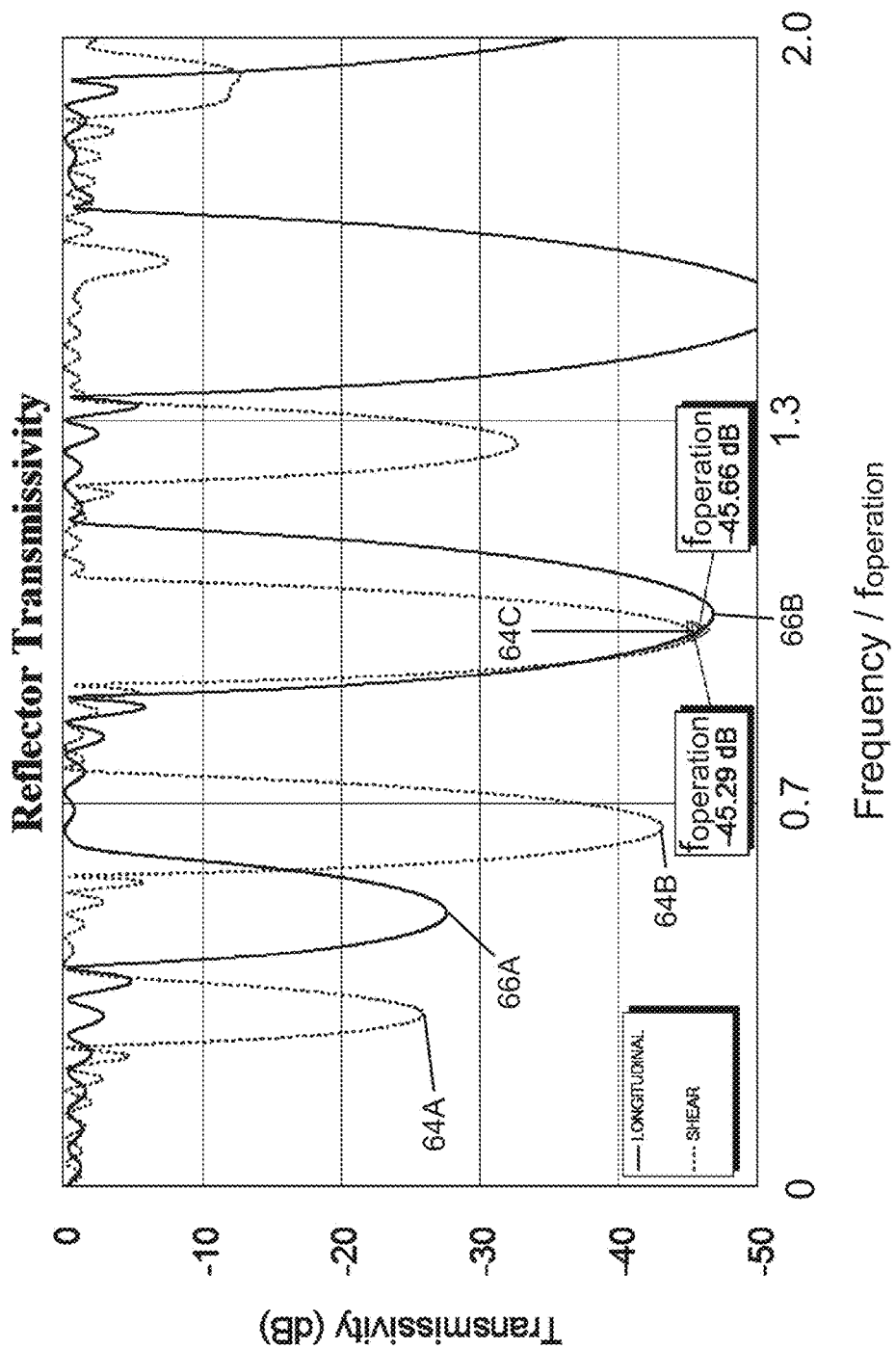
FIG. 7A shows an exemplary transmissivity plot of reflector transmissivity as a function of frequency for an acoustic reflector structure including thirteen layers consisting of alternating $SiO_2/AlN$ layers, with thicknesses of the layers being configured to optimize both shear and longitudinal transmissivity at a desired frequency such that a minimum shear transmissivity at a third harmonic and a minimum longitudinal transmissivity at a second harmonic occur at substantially the same frequency.

FIG. 7A is an exemplary plot of reflector transmissivity as a function of frequency for a thirteen-layer acoustic reflector consisting of alternating layers of $SiO_2$ and AlN forming multiple differential acoustic impedance layer units. As shown, a shear response comprises a first harmonic 64A, a second harmonic 64B, and a third harmonic 64C, and a longitudinal response comprises a first harmonic 66A and a second harmonic 66B. The thicknesses of the reflector layers were configured to optimize both shear and longitudinal transmissivity at a desired frequency such that a minimum transmissivity of the third harmonic 64C of the shear response and a minimum transmissivity of the second harmonic 66B of the longitudinal response occur at substantially similar (or nearly matched) frequencies, thereby creating a significant overlap of the second harmonic 66B of the longitudinal response and the third harmonic 64C of the shear response. Efficiency of an acoustic reflector including alternating low and high impedance layers is related to a difference in acoustic impedance between the respective layers. Comparing the acoustic reflectors of FIGS. 6A and 7A, the difference in acoustic impedance of AlN and $SiO_2$ is about 2.6 times lower than the ratio of W to $SiO_2$, such that the acoustic reflector discussed in connection with FIG. 7A exhibits reduced bandwidth around the frequency of interest and also requires more alternating layers to achieve the desired transmissivity threshold (<40 dB).

FIG. 7B is a table of exemplary thicknesses for each layer of the thirteen-layer acoustic reflector described in connection with FIG. 7A. The thicknesses are defined as fractional multiples of the longitudinal wavelength $\lambda_L$. As shown, the low acoustic impedance material layers (R1, R3, R5, R7, R9, R11, R13) are all of the same material ($SiO_2$) and the same thickness ($0.78*\lambda_L$), and the high acoustic impedance material layers (R2, R4, R6, R8, R10, R12) are all of the same material (AlN) and the same thickness ($0.16*\lambda_L$).

Figure 8A:
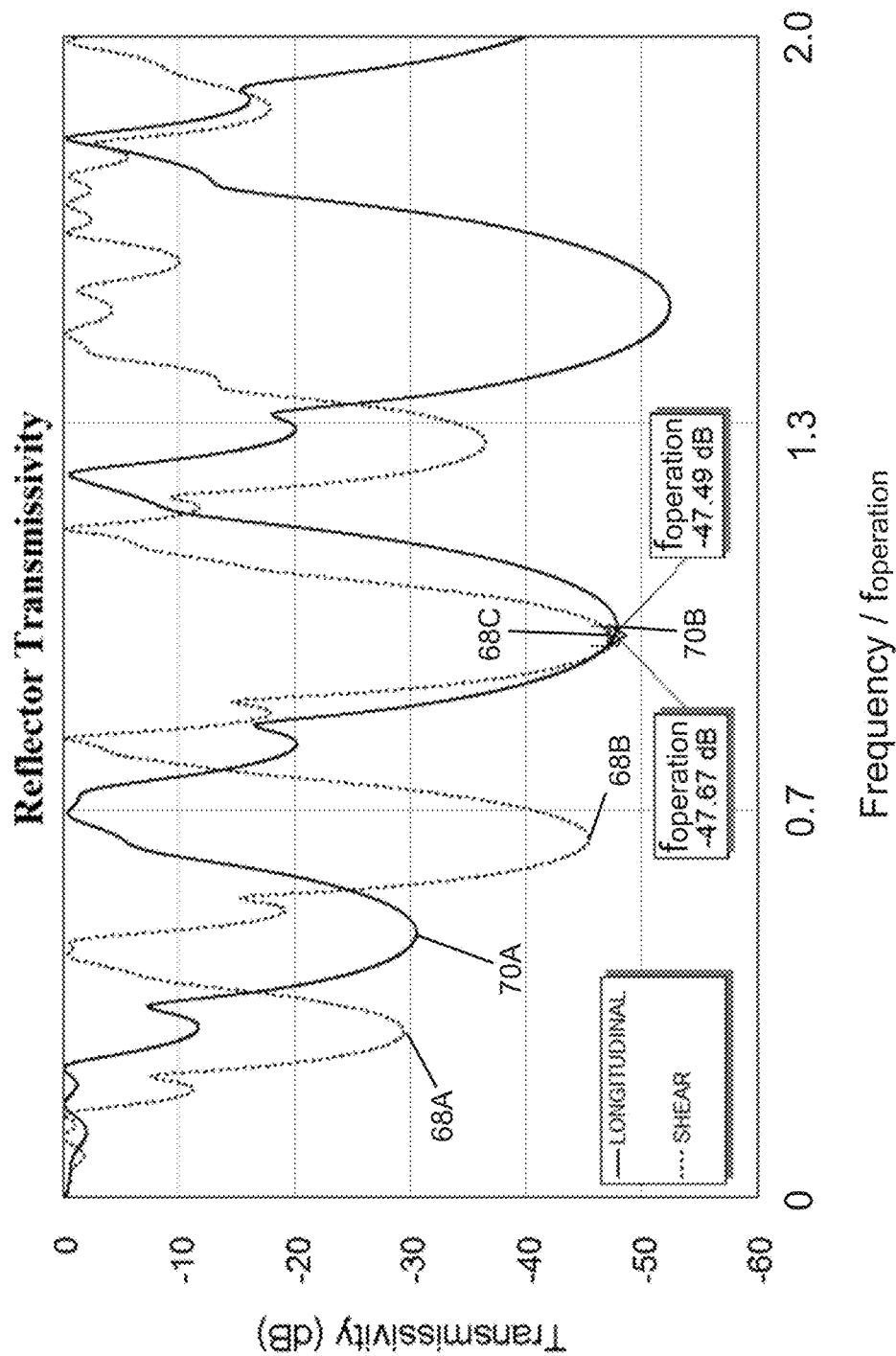
FIG. 8A shows an exemplary transmissivity plot of reflector transmissivity as a function of frequency for an acoustic reflector structure including nine-layer reflector consisting of four alternating $SiO_2/AlN$ layers and five $SiO_2/W$ layers, with thicknesses of the layers being configured to optimize both shear and longitudinal transmissivity at a desired frequency such that a minimum shear transmissivity at a third harmonic and a minimum longitudinal transmissivity at a second harmonic occur at substantially the same frequency.

FIG. 8A is an exemplary plot of reflector transmissivity as a function of frequency for a nine-layer acoustic reflector consisting of four alternating $SiO_2$/AlN layers and five $SiO_2$/W layers forming multiple differential acoustic impedance layer units. As shown, a shear response comprises a first harmonic 68A, a second harmonic 68B, and a third harmonic 68C, and a longitudinal response comprises a first harmonic 70A and a second harmonic 70B. The thicknesses of the reflector layers were configured to optimize both shear and longitudinal transmissivity at a desired frequency such that a minimum transmissivity of the third harmonic 68C of the shear response and a minimum transmissivity of the second harmonic 70B of the longitudinal response occur at substantially matched frequencies, creating a significant overlap of the second harmonic 70B of the longitudinal response and the third harmonic 68C of the shear response. The resulting acoustic reflector structure minimizes transmissivity for both shear and longitudinal modes (e.g., for a given number of layers).

FIG. 8B is a table of exemplary thicknesses for each layer of the nine-layer acoustic reflector described in connection with FIG. 8A. The thicknesses are defined as fractional multiples of the longitudinal wavelength $\lambda_L$. As shown, the low acoustic impedance material layers (R1, R3, R5, R7, R9) are all of the same material ($SiO_2$), but different thicknesses. In particular, low acoustic impedance material layers R1 and R3 are slightly thicker ($0.79*\lambda_L$) than the other low acoustic impedance material layers R5, R7, R9 ($0.76*\lambda_L$). The high acoustic impedance material layers (R2, R4, R6, R8) include multiple different materials and the same thickness. In particular, a first pair of high acoustic impedance material layers R2, R4 are of a first material (W) and a first thickness ($0.16*\lambda_L$), and a second pair of high acoustic impedance material layers R6, R8 are of a second material (AlN) and a first thickness ($0.16*\lambda_L$). The thicknesses of the low acoustic impedance material layers and/or high acoustic impedance material layers may vary in different embodiments depending on the required specifications of the acoustic reflector. The $SiO_2$/AlN layers are all dielectrics and therefore do not require patterning and planarization as is the case for the $SiO_2$/W layers.

FIG. 9 is a table of exemplary low acoustic impedance materials and high acoustic impedance materials for use with acoustic reflector structures according to various embodiments of the present disclosure. Exemplary low acoustic impedance layers 16 include, but are not limited to, silicon oxycarbide [SiOC] (density of 1.5 gm/cm$^3$, acoustic Z of 3.6×10$^5$ gm/cm$^2$ sec), silicon dioxide [$SiO_2$] (density of 2.2 gm/cm$^3$, acoustic Z of 12.9×10$^5$ gm/cm$^2$ sec), polymers (density of 1.0-1.5 gm/cm$^3$). Exemplary high acoustic impedance layers 18 include, but are not limited to, tantalum (IV) oxide [$TaO_2$] (density of 7.6 gm/cm$^3$, acoustic Z of 34.5×10$^5$ gm/cm$^2$ sec), aluminum nitride [AlN] (density of 3.3 gm/cm$^3$, acoustic Z of 35.8×10$^5$ gm/cm$^2$ sec), aluminum oxide [$Al_2O_3$] (density of 3.9 gm/cm$^3$, acoustic Z of 39.8× 10$^5$ gm/cm$^2$ sec), molybdenum [Mo] (density of 10.2 gm/cm$^3$, acoustic Z of 64.3×10$^5$ gm/cm$^2$ sec), and tungsten [W] (density of 19.4 gm/cm$^3$, acoustic Z of 100.6×10$^5$ gm/cm$^2$ sec). Other materials may be used, as will be recognized by one skilled in the art.

Those skilled in the art will recognize improvements and modifications to the preferred embodiments of the present disclosure. All such improvements and modifications are considered within the scope of the concepts disclosed herein and the claims that follow.

What is claimed is:

1. A solidly mounted resonator structure comprising:
    a substrate;
    an acoustic reflector structure arranged over the substrate and comprising a plurality of sequentially arranged differential acoustic impedance layer units, wherein each differential acoustic impedance layer unit of the plurality of sequentially arranged differential acoustic impedance layer units comprises a low acoustic impedance material layer in contact with a high acoustic impedance material layer;
    at least one first electrode structure arranged over at least a portion of the acoustic reflector structure;
    a piezoelectric material layer arranged over the at least one first electrode structure; and
    at least one second electrode structure arranged over at least a portion of the piezoelectric material layer;

wherein:
at least one portion of the piezoelectric material layer is arranged between the at least one first electrode structure and the at least one second electrode structure to form at least one active region;
the solidly mounted resonator structure is configured for transduction of an acoustic wave having a longitudinal wavelength $\lambda_L$ in the at least one active region;
the low acoustic impedance material layer of each differential acoustic impedance layer unit comprises a thickness in a range of from $0.73\lambda_L$ to $0.82\lambda_L$, and
the high acoustic impedance material layer of each differential acoustic impedance layer unit comprises a thickness in a range of from $0.13\lambda_L$ to $0.19\lambda_L$.

2. The solidly mounted resonator structure of claim 1, wherein:
the acoustic reflector structure comprises at least two sequentially arranged differential acoustic impedance layer units and at least one additional low acoustic impedance material layer.

3. The solidly mounted resonator structure of claim 1, wherein the piezoelectric material layer comprises a hexagonal crystal structure piezoelectric material that comprises a c-axis having an orientation distribution that is predominantly non-parallel to normal of a face of the substrate.

4. The solidly mounted resonator structure of claim 1, wherein in each differential acoustic impedance layer unit, the high acoustic impedance material layer comprises an acoustic impedance that is at least about 2.5 times greater than an acoustic impedance of the low acoustic impedance material layer.

5. The solidly mounted resonator structure of claim 1, wherein the substrate is arranged between a backside surface and the acoustic reflector structure, and the backside surface comprises a roughened surface configured to reduce or eliminate backside acoustic reflection.

6. The solidly mounted resonator structure of claim 1, wherein:
the at least one first electrode structure comprises a plurality of first electrode structures;
the at least one second electrode structure comprises a plurality of second electrode structures;
a first portion of the solidly mounted resonator structure comprises a first solidly mounted bulk acoustic wave resonator device including a first active region arranged between one first electrode structure of the plurality of first electrode structures and one second electrode structure of the plurality of second electrode structures; and
a second portion of the solidly mounted resonator structure comprises a second solidly mounted bulk acoustic wave resonator device including a second active region arranged between another first electrode structure of the plurality of first electrode structures and another second electrode structure of the plurality of second electrode structures.

7. A solidly mounted bulk acoustic wave resonator chip derived from the solidly mounted resonator structure of claim 6.

8. A sensor or microfluidic device incorporating the solidly mounted bulk acoustic wave resonator chip of claim 7.

9. A solidly mounted resonator structure comprising:
a substrate;
an acoustic reflector structure arranged over the substrate and comprising a plurality of sequentially arranged differential acoustic impedance layer units, wherein each differential acoustic impedance layer unit of the plurality of sequentially arranged differential acoustic impedance layer units comprises a low acoustic impedance material layer in contact with a high acoustic impedance material layer;
at least one first electrode structure arranged over at least a portion of the acoustic reflector structure;
a piezoelectric material layer arranged over the at least one first electrode structure; and
at least one second electrode structure arranged over at least a portion of the piezoelectric material layer;
wherein:
at least one portion of the piezoelectric material layer is arranged between the at least one first electrode structure and the at least one second electrode structure to form at least one active region;
the solidly mounted resonator structure is configured for transduction of an acoustic wave including a longitudinal component and a shear component in the at least one active region, whereby the piezoelectric material layer exhibits first and second harmonic resonances of a longitudinal response and exhibits first, second, and third harmonic resonances of a shear response; and
a frequency corresponding to a minimum transmissivity of the second harmonic resonance of the longitudinal response is substantially matched to a frequency corresponding to a minimum transmissivity of the third harmonic resonance of the shear response.

10. The solidly mounted resonator structure of claim 9, wherein the frequency corresponding to a minimum transmissivity of the second harmonic resonance of the longitudinal response is within about 5% of the frequency corresponding to a minimum transmissivity of the third harmonic resonance of the shear response.

11. The solidly mounted resonator structure of claim 9, wherein the acoustic reflector structure comprises first, second, and third low acoustic impedance material layers and comprises first and second high acoustic impedance material layers.

12. The solidly mounted resonator structure of claim 9, wherein the piezoelectric material layer comprises a hexagonal crystal structure piezoelectric material that comprises a c-axis having an orientation distribution that is predominantly non-parallel to normal of a face of the substrate.

13. The solidly mounted resonator structure of claim 9, wherein:
the acoustic wave comprises a longitudinal wavelength $\lambda_L$;
the low acoustic impedance material layer of each differential acoustic impedance layer unit comprises a thickness in a range of from $0.73\lambda_L$ to $0.82\lambda_L$, and
the high acoustic impedance material layer of each differential acoustic impedance layer unit comprises a thickness in a range of from $0.13\lambda_L$ to $0.19\lambda_L$.

14. The solidly mounted resonator structure of claim 9, wherein in each differential acoustic impedance layer unit, the high acoustic impedance material layer comprises an acoustic impedance that is at least about 2.5 times greater than an acoustic impedance of the low acoustic impedance material layer.

15. The solidly mounted resonator structure of claim 9, wherein the substrate is arranged between a backside surface and the acoustic reflector structure, and the backside surface comprises a roughened surface configured to reduce or eliminate backside acoustic reflection.

16. The solidly mounted resonator structure of claim 9, wherein:

the at least one first electrode structure comprises a plurality of first electrode structures;

the at least one second electrode structure comprises a plurality of second electrode structures;

a first portion of the solidly mounted resonator structure comprises a first solidly mounted bulk acoustic wave resonator device including a first active region arranged between one first electrode structure of the plurality of first electrode structures and one second electrode structure of the plurality of second electrode structures; and a second portion of the solidly mounted resonator structure comprises a second solidly mounted bulk acoustic wave resonator device including a second active region arranged between another first electrode structure of the plurality of first electrode structures and another second electrode structure of the plurality of second electrode structures.

17. A solidly mounted bulk acoustic wave resonator chip derived from the solidly mounted resonator structure of claim 16.

18. A sensor or microfluidic device incorporating the solidly mounted bulk acoustic wave resonator chip of claim 17.

* * * * *